(12) United States Patent
Gabriel (10) Patent No.: US 6,183,969 B1
(45) Date of Patent: Feb. 6, 2001

(54) INTRON-BASED ASSAY FOR DETECTING AND CHARACTERIZING CHROMOSOMAL REARRANGEMENT

(75) Inventor: Abram Gabriel, Princeton, NJ (US)

(73) Assignee: Rutgers, The State University of New Jersey, New Brunswick, NJ (US)

(*) Notice: Under 35 U.S.C. 154(b), the term of this patent shall be extended for 0 days.

(21) Appl. No.: 09/293,569

(22) Filed: Apr. 15, 1999

(51) Int. Cl.[7] .......................................... C12Q 1/68

(52) U.S. Cl. .................................................. 435/6

(58) Field of Search ................................ 435/6, 325, 441, 435/463

(56) References Cited

PUBLICATIONS

Sargent et al., *Mol. Cell. Biol.,* vol. 17, Jan. 1997, pp. 267–277*

* cited by examiner

*Primary Examiner*—James Ketter
(74) *Attorney, Agent, or Firm*—Law Offices of Jane Massey Licata (57) ABSTRACT

An assay is provided for detecting and characterizing chromosomal rearrangements in eukaryotic cells by genetically engineering a eukaryotic cell to contain a selectable/counterselectable marker gene with a site for generating a double strand break within an intron of the eukaryotic cell; generating the double strand break; detecting cells which repair the double strand break by chromosomal rearrangements; isolating DNA from the detected cells; and characterizing the chromosomal rearrangement as a nonhomologous translocation, inversion, deletion or insertion.

8 Claims, 2 Drawing Sheets

SEQUENCE LISTING

```
<160> NUMBER OF SEQ ID NOS: 14

<210> SEQ ID NO 1
<211> LENGTH: 27
<212> TYPE: DNA
<213> ORGANISM: Artificial Sequence
<220> FEATURE:
<223> OTHER INFORMATION: Description of Artificial Sequence:Synthetic

<400> SEQUENCE: 1
gatctacgta tgttctagcg cttgcac                                        27

<210> SEQ ID NO 2
<211> LENGTH: 28
<212> TYPE: DNA
<213> ORGANISM: Artificial Sequence
<220> FEATURE:
<223> OTHER INFORMATION: Description of Artificial Sequence:Synthetic

<400> SEQUENCE: 2
gatctagcta aacatataat atagcaac                                       28

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence:Synthetic
```

<400> SEQUENCE: 3
tgttagcggt ttgaagcagg                                           20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 4
ttctccagta gatagggagc                                           20

<210> SEQ ID NO 5
<211> LENGTH: 41
<212> TYPE: DNA
<213> ORGANISM: Artificial Sequence
<220> FEATURE:
<223> OTHER INFORMATION: Description of Artificial Sequence:Synthetic

<400> SEQUENCE: 5
cccggagctc gagctcgatc taaataaatt cgttttcaat g                   41

<210> SEQ ID NO 6
<211> LENGTH: 33
<212> TYPE: DNA
<213> ORGANISM: Artificial Sequence
<220> FEATURE:
<223> OTHER INFORMATION: Description of Artificial Sequence:Synthetic

<400> SEQUENCE: 6
gggcgagctc gagctcaacc actctacaaa acc                            33

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence:Synthetic

<400> SEQUENCE: 7
gcgaggcata tttatggtga agg                                       23

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence:Synthetic

<400> SEQUENCE: 8
gtacatgaga cttagtaaca gtagc                                     25

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence:Synthetic

<400> SEQUENCE: 9
atgttctagc gcttgcacca tc                                        22

<210> SEQ ID NO 10
<211> LENGTH: 19

```
<212> TYPE: DNA
<213> ORGANISM: Artificial Sequence
<220> FEATURE:
<223> OTHER INFORMATION: Description of Artificial Sequence:Synthetic

<400> SEQUENCE: 10
ggagttcaat gcgtccatc                                                19

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence:Synthetic

<400> SEQUENCE: 11
tttcaagccc ctatttattc c                                             21

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 12
agcgtctgct ctagcgttac                                               20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 13
gtagagggtg aacgttacag                                               20

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence:Synthetic

<400> SEQUENCE: 14
cagtcaatat aggaggttat g                                             21
```

INTRON-BASED ASSAY FOR DETECTING AND CHARACTERIZING CHROMOSOMAL REARRANGEMENT

INTRODUCTION

This invention was supported in part by funds from the U.S. government (NIH Grant No. R29AI39201) and the U.S. government may therefore have certain rights in the invention.

FIELD OF THE INVENTION

The present invention relates to a powerful assay for detecting and characterizing chromosomal rearrangements in eukaryotic cells. Using this assay, environmental factors such as drugs, genetic factors such as specific gene mutations, as well as the presence or absence of specific DNA segments can all be examined for their role in promoting chromosome instability via nonhomologous recombination.

BACKGROUND OF THE INVENTION

Cancer is a genetic disorder in which a series of mutations subvert the normal developmental program of a cell and allow it to proliferate without constraint. Accumulation of deleterious mutations appear to represent the basis of cancer progression (Kinzler, K. W. and Vogelstein, B. *Nature* 1997 386:761–763). While these mutations can take many forms, the most characteristic form of genetic change in cancer cells is karyotypic instability with aneuploidy and chromosomal rearrangements, particularly balanced translocations. By joining together previously unlinked chromosomal arms, balanced translocations can result in the creation of hybrid genes with altered expression patterns for potential oncogenes or tumor suppressor genes. Karyotypic detection of translocations has been very useful for cancer researchers. Clinically, the presence or absence of specific translocations has therapeutic and prognostic implications. More fundamentally, genes identified at the translocation breakpoints are strong candidates for involvement in malignant transformation (Sanchez-Garcia, I. *Annu. Rev. Genet.* 1997 31:429–453). These translocations serve as markers of the malignant state and can be either the cause or the consequence of the transformed state. For example, the Philadelphia chromosome is a specific t(9;22)(q34;q11) translocation that fuses the B-cell antigen receptor gene BCR and the ABL oncogene (De Klein et al. *Nature* 1982 300: 765–767). This fusion is thought to represent the crucial event in the development of chronic granulocytic leukemia. However, this translocation can also appear later in the course of multiple forms of leukemia. In general, it appears that all hematologic malignancies originate from such "dangerous liaisons" between unlinked chromosomal segments. Solid tumors as well may have characteristic translocations, suggesting that the development of an unstable chromosomal state increases the likelihood of translocations which in turn increase the likelihood of tumor progression (Rabbitts, T. H. *Nature* 1994 372:143–149; Sanchez-Garcia, I. *Annu. Rev. Genet.* 1997 31:429–453).

While the identification and analysis of the genes present at specific translocation breakpoints has become an area of great research interest, causes of these translocations are still poorly understood. Clearly an understanding of possible causes, however, is important for cancer prevention, for identification of at risk individuals, and for developing potential targets of drug intervention.

Translocations are believed to arise by recombination, a descriptive term given to any process whereby double-stranded DNAs are broken and rejoined in ways that alter the linkage relationship of the genes near the breaks. At least three different recombination pathways that operate in cells which can cause translocations have been proposed.

First, during homology-dependent or homologous recombination, identical sequences on nonhomologous chromosomes are believed to crossover, resulting in new linkages of nonhomologous chromosome arms. This model is supported by the fact that repetitive sequences in the human genome such as Alu elements or retrotransposons such as LINE elements are occasionally observed at translocation breakpoints (Kato et al. *Gene* 1991 97:239–244). Studies from a number of model organisms, particularly *Saccharomyces cerevisiae*, indicate that the presence of a double strand break (DSB) greatly stimulates the process of homologous recombination, via strand invasion of a linear single-stranded end into complementary double-stranded sequences elsewhere in the genome (Petes et al. (1991) Recombination in yeast. "The Molecular and Cellular Biology of the yeast Saccharomyces". Broach, J. R., Pringle, J. R. and Jones, E. W., Cold Spring Harbor Laboratory Press, Cold Spring Harbor, N.Y.). Model systems for homology-directed transpositions have been developed in yeast and in mammalian cells which take advantage of the stimulatory effect of an induced DSB (Fasullo et al. *Mutat Res.* 1994 314:121–133; Haber, J. E. and Leung, W. *Proc. Natl. Acad. Sci. USA* 1996 93:13949–13954; and Richardson et al. *Genes & Dev.* 1998 12:3831–3842). However, it appears that homologous recombination is at best a minor pathway for translocation-formation in human cancers.

Site-specific recombination requiring a site-specific recombinase, as well as specific DNA recognition sequences, have also been proposed. In humans, B and T cell precursors go through a site-specific recombinational process known as V(D)J rejoining that is essential to their maturation. V(D)J rejoining assembles antigen receptor variable genes by making DSBs at specific recombination signal sequences and then rejoining non-contiguous intrachromosomal segments. Many reciprocal translocations associated with lymphoid malignancies involve a V(D)J cleavage-rejoining site at the breakpoint (Rabbitts, T. H. *Nature* 1994 372:143–149). This has led to the concept that these translocations result from aberrant nonhomologous rejoining events during this normally site-specific process. The V(D)J cleavage site represents one break. Potential sources of the second break include both physiological (e.g. transcription, replication, repair) and environmental (e.g. x-rays, free radicals). In these cases, the V(D)J break might be joined to another simultaneous break. It was recently demonstrated that the V(D)J recombinase can function as a transposase, capable of actively inserting cleaved DNA ends into random targets (Hiom et al. *Cell* 1998 94:463–470). Similar experimental systems using other site-specific recombinases have also been designed that can generate recombinase-dependent translocations in the presence of a recombinase and appropriate recognition sequences on separate nonhomologous chromosomes (Golic, K. G. and Lindquist, S. *Cell* 1989 59:499–509; Sauer, B. *J. Mol. Biol.* 1992 223:911–928; and Van Deursen et al. *Proc. Natl. Acad. Sci. USA* 1995 92:7376–7380).

Nonhomologous recombination is an inherently imprecise form of recombination that appears to be the major pathway for DSB repair in human cells (Meuth, M. (1989) Illegitimate recombination in mammalian cells. "Mobile DNA". Berg, D. E. and Howe, M. M., American Society for Microbiology, Washington, D.C.; and Roth, D. and Wilson, J. (1988) Illegitimate recombination in mammalian cells.

"Genetic Recombination". Kucherlapati, R. and Smith, G. R., American Society for Microbiology, Washington, D.C.), although it represents a minor pathway in *Saccharomyces cerevisiae* (Haber, J. E. *Bioessays* 1995 17:609–620). In this form of recombination, no special sequences are present at the break sites. Instead variable length deletions or rearrangements have been observed at break sites. The recombination joints normally involve at most, a few (<5) overlapping bases. Based on analysis of breakpoints, it is believed that most cancer-causing chromosomal translocations occur by nonhomologous end-joining of simultaneous DSBs that are present on separate nonhomologous chromosomes. This type of recombination has been studied in mammalian systems by analyzing sites of integration and excision of DNA viruses and transfected linear marker DNA, as well as by determining the genetic components required for the normal recombinational repair of V(D)J site-specific cleavage events (Roth et al. *Current Biol.* 1995 5:496–499). Further information has come from studies in *Saccharomyces cerevisiae*. The data so far suggests that there may be multiple end-joining pathways which utilize (amongst other proteins) Rad50, Mre11, Xrs2, Ku70, Ku80, the DNA-dependent protein kinase, DNA ligase 4, and XRCC4p (Hendrickson, E. A. *Am. J. Hum. Genet.* 1997 61:795–800).

The underlying causes of the translocations found in human tumors are believed to result from physiological, genetic, and/or environmental conditions which increase DSBs or decrease their repair thereby predisposing the cells to translocation formation. For example, lymphoid malignancies have associated translocations involving V(D)J recombination sites (Finger et al. *Science* 1986 234:982–985). The fact that V(D)J rejoining is a normal developmental process limited to lymphoid precursor cells underscores the point that the presence of a DSB at a specific chromosomal site makes that site a hotspot for translocations. As another example, several rare recessive human disorders have been identified, including Bloom's Syndrome, ataxia telangiectasia, and Nijmegen Breakage Syndrome, whose hallmarks are chromosomal instability, hypersensitivity to DNA damaging agents, and early onset of a variety of malignancies. Analysis of the genes that are defective in these syndromes suggests that their normal functions are to minimize natural DSBs or to halt progression of the cell cycle until DSBs are repaired (Brown et al. *Proc. Natl. Acad. Sci. USA* 1997 94:1840–1845; Carney et al. *Cell* 1998 93:477–486; Chaganti et al. *Proc. Natl Acad. Sci. USA* 1974 71:4508–12; Ellis et al. *Cell* 1995 83:655–666; Epstein et al. *Medicine* 1966 45:177–221; Kasten et al. *Cell* 1992 71:587–597; Krepinsky et al. *Human Genetics* 1979 50:151–6; Varon et al. *Cell* 1998 93:467–476; Watt et al. *Genetics* 1996 144:935–945; and Yamagata et al. *Proc. Natl. Acad. Sci., USA* 1998 95:8733–8738). In their absence, higher levels of DSBs can accumulate and be anomalously rejoined. Ionizing radiation is a well known environmental factor that damages DNA, in part by causing DSBs. The occurrence of leukemias and other malignancies in individuals exposed to high levels of radiation underscores this connection. More commonly, individuals treated with a wide range of cancer chemotherapeutic agents are at high risk for development of treatment-related malignancies, particularly acute myeloid and acute lymphoblastic leukemias (Rowley et al. *N Engl J Med* 1996 334: 601–603).

The presumed mechanism of action of many anticancer drugs is that they cause multiple DSBs, thereby triggering apoptosis. One particularly interesting class of drugs are the epipodophyllotoxins which target topo II. Topo II untangles long strands of DNA by cleaving double-stranded DNA via a covalently-bound intermediate, allowing passage of an intact DNA duplex through this break, and then rejoining the cleaved ends. Anti-topo II drugs that are associated with treatment-related leukemias are thought to function by stabilizing the broken DNA state and inhibiting the rejoining step. Thus, while accumulation of enzyme-induced DSBs may lead to apoptotic cell death in some cells, it may also result in reciprocal translocations in others.

Thus, these observations support a general model of translocation formation involving aberrant repair of DSBs. However, with respect to cancer causing translocations, it is still unknown whether DSB formation and subsequent rejoining is essentially a random process or whether factors influence the susceptibility of certain sequences and chromosomal regions to breakage and rejoining. The identification of factors which influence the likelihood of a translocation to occur at a specific chromosomal locus will lead to approaches to prevent specific rearrangements and to identify them at an early stage.

A hamster cell system has been designed in which the recognition sequence for the rare cutting endonuclease I-SceI was placed in the second intron of a hemizygous adenine phosphoribosyltransferase (APRT) gene (Sargent et al. *Mol. Cell. Biol.* 1997 17:267–277). In this hamster cell system, a constitutive I-SceI expression vector was used to generate cleavages at the cut site, and aprt– clones were recovered by growth on 8-aza-adenine. Using this system, illegitimate recombination events were detected. However, chromosomal rearrangements associated with the illegitimate recombination events were not characterized in these experiments.

In the present invention, an assay is provided for detecting nonhomologous translocations in eukaryotic cells including yeast and mammalian cells.

SUMMARY OF THE INVENTION

An object of the present invention is to provide an assay for detecting chromosomal rearrangements including nonhomologous translocations, inversions, deletions and insertions in eukaryotic cells. Cells used in this assay are genetically engineered to contain a site for generating a double strand break in an intron within a selectable/counter-selectable marker gene so that, upon generating the double strand break, cells incapable of repairing the break die; cells which repair the break by simple reattachment of the two ends or by homologous recombination are not detected; and cells which repair the break by chromosomal rearrangements that disrupt the expression of the marker gene are detected. DNA of the detected cells is then isolated and the nature of the rearrangement is determined.

In one embodiment, prior to or concurrent with generating the double strand break in the genetically engineered cells, the cells are exposed to environmental factors such as drugs to ascertain the effects of the drug on chromosomal rearrangement. Alternatively, a selected gene of the genetically engineered strain is mutated or overexpressed prior to generating the double strand break to ascertain the effects of this mutation on chromosomal rearrangement.

DETAILED DESCRIPTION OF THE INVENTION

Chromosome instability is a hallmark of cancer cells. Balanced translocations, in which arms of nonhomologous chromosomes are joined to one another at specific breakpoints, are distinctive characteristics of certain malignancies and may represent causative genetic events. Little is known, however, about the factors that predispose chromosomes to translocate or the mechanisms by which specific translocations are generated within cells.

In the present invention an assay is provided for detection of chromosomal rearrangements including nonhomologous translocations, inversions, deletions and insertions in eukaryotic organisms. For this assay eukaryotic cells are genetically modified or engineered to contain a selectable/counter-selectable marker gene with a site for generating a double strand break (DSB) within an intron of the eukaryotic cell. In a preferred embodiment, this is done by inserting a restriction site for a rare cutting enzyme into an intron within a marker gene. The DSB is then generated, preferably via inducing expression of the rare cutting enzyme, in the cells. The basis for the assay of the present invention is that a DSB is made in an intron within a selectable/counter-selectable marker gene in a way that most cells will be incapable of repairing the break and will therefore die. Those that do repair the break by simple reattachment of the two ends or by homologous recombination will not be detected by the counterselection scheme. However, those cells which repair the break by chromosomal rearrangements that disrupt the expression of the marker gene will be detected. DNA from the detected cells can then be isolated to determine the nature of the rearrangement, i.e. nonhomologous translocation, inversion, deletion or insertion, preferably via PCR analysis. The utility of this assay is that environmental factors such as drugs, genetic factors such as specific gene mutations, as well as the presence or absence of specific DNA segments can all be examined for their role in promoting chromosome instability via nonhomologous recombination. Most individual features of this method are generic and can therefore be modified to meet the particular needs of the investigator.

Saccharomyces cerevisiae has been among the most important organisms to study recombinational processes in eukaryotes (Petes et al. (1991) Recombination in yeast. "The Molecular and Cellular Biology of the yeast Saccharomyces". Broach, J. R., Pringle, J. R. and Jones, E. W., Cold Spring Harbor Laboratory Press, Cold Spring Harbor, N.Y.). Its utility as an experimental organism is based in part on its small size, simple nutrient requirements, rapid doubling time, the wealth of genetic markers available for each chromosome, its ability to be studied in both a haploid or diploid form, and most recently by the fact that it has been completely sequenced. Consequently, the position of every gene on every chromosome is known to nucleotide resolution (Botstein et al. Science 1997 277:1259–1260).

Yeast carries out the same basic cellular processes as human cells, and in many cases human homologs have been used to complement deficiencies in essential yeast genes. This has allowed for the functional analysis of human genes in yeast. Segments of human DNA are routinely maintained as yeast artificial chromosomes (YACs). Further, many clinically relevant human genes were first identified as homologs to genes previously identified in yeast.

Studies by various researchers have demonstrated the value of studying topoisomerases in yeast cells (Reid et al. Biochim Biophys Acta 1998 400:289–300). Yeast encodes two, non-essential type I topoisomerases (TOP1 and TOP3) and a single essential type II topoisomerase (TOP2). Deletion mutations of TOP1 or TOP3 have decreased genomic stability as indicated by hyper-recombination of naturally occurring direct repeat regions (Christman et al. Cell 1989 55:413–425; Kim, R. A. and Wang, J. C. Cell 1989 57:975–85; Wallis et al. Cell 1989 58:409–419). Overexpression of yeast or human TOP1 results in hypersensitivity to anti-topo I drugs (Bjornsti et al. Cancer Res 1989 49:6318–6323). TOP2 is an essential gene, but temperature sensitive alleles are available. Prolonged TOP2 overexpression on an inducible GAL promoter is lethal (Worland, S. T. and Wang, J. C. J. Biol. Chem. 1989 264:4412–4416). Yeast TOP2 deletions can be complemented by human topo II genes (Wasserman et al. Cancer Res. 1993 53:3591–3596). This means that studies of factors specifically affecting human topo II can be carried out in yeast. Yeast cells can be made sensitive to topoisomerase inhibitor drugs by mutations in genes involved in cell membrane biosynthesis or multidrug resistance (Balzi, E. and Goffeau, A. J. Bioenerg. Biomembr. 1995 27:71–76; Nitiss, J. and Wang, J. C. Proc. Natl. Acad. Sci. USA 1988 85:7501–5; Nitiss et al. Annals of the New York Academy of Sciences 1996 808:32–43; and Reid et al. J Biol Chem 1997 272:12091–12099) allowing study of drug effects in yeast.

Although recombination, particularly homologous recombination, has been intensively studied in Saccharomyces, studies on the formation of translocations have been limited. The natural occurrence of reciprocal translocations was inferred from genetic studies. Their appearance has also been reported, along with other chromosomal rearrangements, in association with transposon insertions (Roeder et al. Science 1980 209:1375–1380; Roeder, G. S. and Fink, G. R. Cell 1980 21:239–249). Most studies of translocation formation in yeast are based on directing recombination between homologous sequences on nonhomologous chromosomes (Chen et al. Molecular Cell 1998 2:9–22; Fasullo et al. Mol. Cell. Biol. 1998 18:1190–1200; Fasullo et al. Mutat Res. 1994 314:121–133; Gerring et al. Methods Enzymol. 1991 194:57–77; Haber, J. E. and Leung, W. Proc. Natl. Acad. Sci. USA 1996 93:13949–13954). While these studies demonstrate the ability and ease of generating homology-dependent chromosomal translocations, they have not concentrated on the class of nonhomologous events that account for the majority of human chromosomal rearrangements.

The assay of the present invention, initially developed in yeast due to the vast amount of information already available for this eukaryotic organism, provides an efficient means of detecting nonhomologous translocations in eukaryotic organisms. This assay thus provides a new means of probing the mechanisms underlying this important process.

Figure 1:
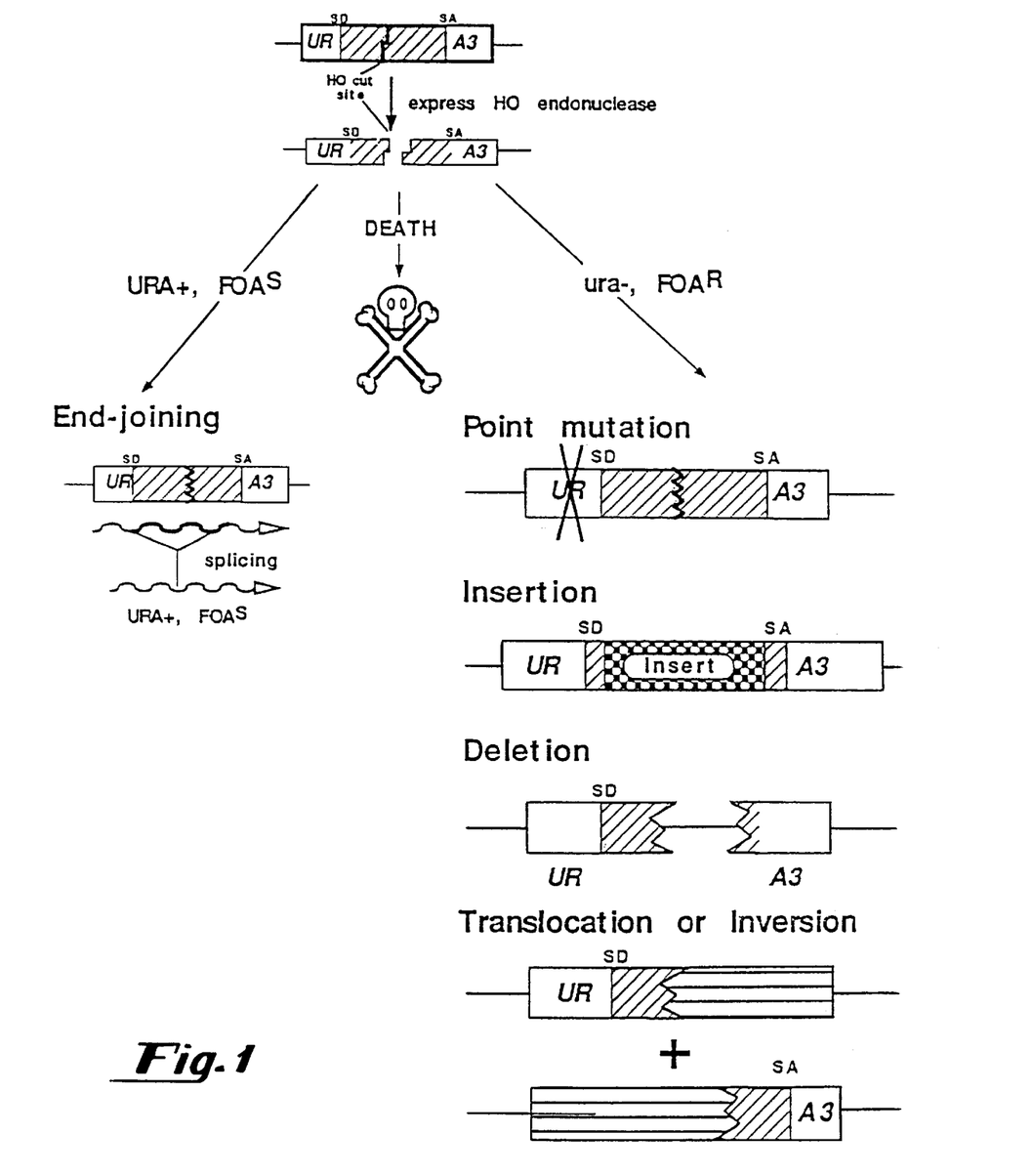
FIG. 1 provides a schematic of a yeast based assay of the present invention referred to as the URA3::actin intron assay.

In initial experiments, a yeast-based assay was developed as depicted in FIG. 1 to directly select for potential cDNA insertions occurring after inducing a specific DSB. This assay is referred to herein as the "URA3::actin intron assay". Using this assay, endogenous Ty1 insertion events at a DSB have been readily identified. Further, it has been found that this assay can easily detect rare large-scale genomic rearrangements, particularly reciprocal translocations. These translocations appear to be the products of nonhomologous end-joining events, like their counterparts in human cancer cells. Thus, the yeast based assay provides a unique opportunity to study translocation formation by nonhomologous pathways in a genetically tractable system.

As shown in FIG. 1, the URA3::actin intron assay was developed by engineering a URA3 allele to contain a copy of the 310 base yeast actin intron. The presence of the intron does not interfere with URA3 expression, because it is precisely spliced from the resulting RNA. A 132 base sequence from the MATa locus, which contains the recognition sequence for the HO endonuclease, 60 bases downstream of the actin intron splice donor site was also inserted. Again, the presence of this additional sequence does not affect URA3 expression, since the sequences within the intron are irrelevant as long as they do not interfere with the essential splice donor, splice acceptor or branch point acceptor sites. The URA3 gene was chosen for these initial experiments because its expression can be selected for (by growth in media lacking uracil) or selected against (by growth on media containing 5-fluoro orotic acid (FOA)). Cells which express URA3 are killed by a toxic product of FOA metabolism and are said to be FOA sensitive (FOA$^S$). Cells not expressing URA3 can survive on such media and are said to be FOA resistant (FOA$^R$).

The basis for the assay of the present invention is that a DSB can be uniquely, precisely, and efficiently generated within the URA3::actin intron::HO cut site region by inducing expression of HO endonuclease under the control of a GAL1 promoter. This is a lethal event unless the break is repaired by some form of nonhomologous recombination. Repair by homologous recombination is not possible because there is no homology to the cut site elsewhere in the genome. The surviving cells are secondarily selected for loss of URA3 expression by plating on FOA-containing media. Because the DSB occurs within a non-functional segment of DNA (i.e. the middle of an intron), repair by imprecise rejoining of the broken ends will not affect URA3 expression. However, events that make the intron unsplicable, such as insertions or deletions which affect the size of the intron or remove splicing signals, as well as translocations which separate the two chromosome arms, will all result in FOA resistance. The frequency of appearance of FOA$^R$ colonies is determined and individual FOA$^R$ colonies are analyzed by PCR and/or Southern blots and by sequencing to determine the nature of the rearrangements.

The haploid yeast strains used for these studies are described in Example 1. In these strains all sequences homologous to the HO cut site have been deleted. Instead, the strains carry a copy of HO endonuclease under the control of a galactose-inducible promoter at the ADE3 locus. When galactose is added to the media, HO is expressed and DSBs are efficiently generated (Haber, J. E. *Bioessays* 1995 17:609–620; White, C. I. and Haber, J. E. *EMBO J.* 1990 9:663–637).

The ability of the URA3::actin intron assay to detect repair events that involve chromosomal rearrangements was determined. In these experiments, cells from three different genetic backgrounds and with 0, 1, or 2 HO cut sites, were grown on either galactose (DSB-inducing) or glucose (non-inducing) plates. Survival on galactose was approximately 0.27–1.5% in the presence of a single cut site, but varied from $10^{-6}$ to approximately $10^{-3}$ in strains with two cut sites. Strains used were either wild type for recombinational repair, defective in the homologous repair pathway (rad52) or defective in the nonhomologous end-joining pathway (ku80). Given the lower survival of ku80 cells, it appears that under the experimental conditions used the nonhomologous repair pathway is the more important pathway for handling chromosomal breaks.

Colonies growing on galactose plates were replica plated to FOA-containing plates. In the absence of an HO cut site in the URA3 gene, the frequency of spontaneous FOA resistance is $<1\times10^{-7}$. However, the frequency of FOA resistance amongst survivors varied from approximately 1 to 34%, with the highest frequency occurring in the rad52 double cut site strain. Genomic DNA was extracted from FOA resistant colonies and the events associated with survival were examined by PCR amplification of the URA3 gene, using primers on either side of the HO cut site. Four classes of PCR products were recovered. Those that were smaller than the original band had deleted sequences around the cut site. Those equivalent in size to the original band were believed to result from point mutations in the URA3 coding region. Those that were larger than the original band were due to insertions at the cut site. Finally, there was a class without observable PCR products. The relative proportion of each these classes in different strain backgrounds is shown in the following Table.

| Strain | Class of PCR product | PCR Result | Analysis |
|---|---|---|---|
| Wild type, single cut site | deletion | 1/12 | |
| | no change | 1/12 | |
| | insertion | 3/12 | all Ty1 insertions |
| | no product | 7/12 | 3 translocations; 2 Ty1 insertions; 2 unknowns |
| Wild type, double cut site | deletion | 0/12 | |
| | no change | 0/12 | |
| | insertion | 0/12 | |
| | no product | 12/12 | 9 translocations; 3 unknowns |
| rad52, single cut site | deletion | 0/12 | |
| | no change | 1/12 | |
| | insertion | 4/12 | 2 Ty1 insertion; 2 mito. DNA inserts |
| | no product | 7/12 | 1 translocation; 2 insertions; 4 unknowns |
| rad52, double cut site | deletion | 0/12 | |
| | no change | 0/12 | |
| | insertion | 0/12 | |
| | no product | 12/12 | all translocations |
| ku80, single cut site | deletion | 72/80 | all actin intron gene conversions |
| | no change | 0/80 | |
| | insertion | 0/80 | |
| | no product | 8/80 | variable length intrachromosomal deletions |

A combination of Southern blot analysis and inverse PCR was used to screen a large number of FOA$^R$ colonies that do not PCR amplify using two primers in URA3. It was found that some of the PCR-negative FOA$^R$ colonies are large deletions (ku80 strain) or large Ty1 insertions (e.g. WT and rad52 single cut site strains). Many others, however, represent translocations and inversions. For example, the same pericentric inversion of chromosome V was independently recovered four times from both WT and rad52 strains. In these independent events the precise junctional sequences and overlaps at the breakpoints are slightly different but are clearly from the same 6 base region. This second site on chromosome V, approximately 200 kb from the URA3 locus, is believed to constitute a cryptic cleavage site for the HO endonuclease, since the original sequence around the breakpoint has 13 of 18 bases identical to the HO cut site. For seven other translocations, no obvious sequence similarity could be identified at the breakpoint on the partner chromosome to the consensus HO recognition sequence (Nickoloff et al. *Mol Cell Biol* 1990 10:1174–1179). A summary of non-insertion chromosomal rearrangements is depicted in the following table.

| | |
|---|---|
| 1. | Pericentric chromosome V inversion (~nt 291,228) × 4; WT and rad52 |
| 2. | Chromosome V:chromosome IV reciprocal translocation (nt 591,695) × 1; WT |
| 3. | Chromosome V:chromosome IV reciprocal translocation (nt 961,049) × 1; rad52 |
| 4. | Chromosome V:chromosome IV reciprocal translocation (nt 521,695) × 2; WT |
| 5. | Chromosome V:chromosome II reciprocal translocation (nt 258,896) × 1; WT |
| 6. | Chromosome V:chromosome II reciprocal translocation (nt 341,565) × 1; WT |
| 7. | Chromosome V:chromosome II reciprocal translocation (nt 555,799) × 1; rad52 |
| 8. | Chromosome V:chromosome XI reciprocal translocation (nt 151,108) × 1; rad52 |
| 9. | Chromosome V deletions (5.2 kb – 13.6 kb telomere proximal to the HO cut site) × 6; ku80 |

Information from identifying one breakpoint was used to design and PCR amplify the reciprocal breakpoint for each strain. From analyzing the junctional data it appears that these translocations are typical nonhomologous end-joining reactions representing simple reciprocal translocations. There are sometimes overlapping microhomologies of <4 bases. There are no large deletions around the breakpoints. In fact, in some cases every base from both break sites can be accounted for. In each case, the partner chromosomal arms are consistent with switching of distal arms, rather than formation of dicentric chromosomes. This result may be a function of the haploid state of this strain, which is less likely to tolerate significant deletion events, as would be expected in the resolution of a dicentric chromosome. The absence of translocations in the ku80 strain and the minimal differences in the FOA$^R$ spectrum for WT and rad52 strains indicate that reciprocal translocation formation in yeast is Rad52-independent but is dependent on the Ku80 protein.

Stimulation of the formation of reciprocal translocations by the simultaneous presence of chromosome cleavages on two different chromosomes was then confirmed using strains with two HO cut sites on different chromosomes. The second HO cut site region was inserted into the LEU2 gene on chromosome III. As expected, survival on galactose for the double cut site strains was lower than the single cut site strains. However, the frequency of FOA resistance amongst survivors was high, particularly in the rad52 strain (34%). In all cases, PCR amplification of the FOA resistant colonies using two URA3 primers was negative. However, almost all gave PCR products when a URA3 primer was partnered with a LEU2 primer. Junctional sequence analysis of the breakpoints from these events revealed that they are a heterogeneous collection of nonhomologous end-joins. In some cases the junctions showed a few bases of addition or deletion, in other cases the joins were precise, and in a few cases there were deletions of approximately 120 bases.

Thus, as shown this assay can easily detect chromosomal rearrangements associated with repair of DSBs. By using appropriate yeast strains, repair events that require homologous recombination pathways are eliminated. With this assay, rare translocations can be easily identified and characterized. Further, the frequency and spectrum of these rearrangements can be studied in detail, and the assay can be modified to accommodate changes in genetic background, changes in the source of the DSB, changes in potential target sequences for rearrangements, or changes in the environment in which the cells are growing. The ability to easily identify and select for reciprocal translocations suggests an obvious and important application of this assay, i.e. to bring to bear the power of yeast genetics and yeast molecular biology to examine mechanisms underlying cancer causing translocations. Accordingly, this yeast model system can contribute greatly to our understanding of the genesis of cancer-causing chromosomal translocations.

For example, the yeast assay of the present invention may be useful in determining the contributions of DNA topoisomerase I (topo I) and topoisomerase II (topo II) to the formation of chromosomal translocations. DNA topoisomerases are ubiquitous nuclear enzymes required for reducing torsional stress during replication, transcription and cell division. These enzymes function by transiently cleaving single- (topo I) or double-stranded DNA (topo II) and then resealing the phosphodiester backbone. The presence of these activities has led to models for nonhomologous recombination between different DNA ends via topoisomerase-mediated mechanisms. Using the present invention, these models can be directly tested in *Saccharomyces cerevisiae* by altering the cellular pool of topoisomerases and determining the consequences this has on survival and translocation formation. Three topoisomerases have been identified in *Saccharomyces cerevisiae* and yeast TOP1 and TOP2 have been extensively characterized. Genetic data indicates that under-expression of TOP1 and/or TOP2 leads to a hyper-recombination phenotype, suggesting that increased numbers of DNA breaks may occur when these enzymes do not optimally carry out their cellular roles of relieving torsional stress during replication, transcription, and cell division (Christman et al. *Cell* 1989 55:413–425; Christman et al. *Proc. Natl Acad. Sci., USA* 1993 90:7637–41; Kim, R. A. and Wang, J. C. *Cell* 1989 57:975–85). Alternatively, overexpression of topoisomerases in yeast make them hypersensitive to anti-topoisomerase drugs which stabilize enzyme-DNA cleavable complexes (Bjornsti et al. *Cancer Res.* 1989 49:6318–6323; Nitiss et al. *Cancer Res.* 1992 52:4467–4472). Therefore the genetic tools are available to use the yeast system to analyze in detail the relationship between topoisomerases and the formation of break induced nonhomologous recombination events.

The URA3::actin intron::HO cut site system of the present invention greatly increases the ability to study these events. For these experiments isogenic yeast strains differing only in mutations or overexpression of a single gene are generated. In one embodiment, TOP1 is specifically deleted using standard deletion technology (Alani et al. *Genetics* 1987 116:541–545; Rothstein, R. *Methods Enzymol.* 1991 194:281–301; Wach et al. *Yeast* 1994 10:1793–1808). Since TOP2 is an essential gene, this gene can not be deleted. Instead, its expression is decreased by two different approaches. First, the WT gene is replaced with an available temperature sensitive TOP2 allele, whose expression can be regulated by growing cells at different semi-permissive temperatures. Second, the endogenous TOP2 is replaced with a plasmid-based TOP2 gene under an inefficiently transcribed promoter that keeps the cells alive but limits the level of TOP2 in the cell. Multiple approaches can be used for overexpression studies. For example, the TOP1 and TOP2 genes can be placed on high copy 2 micron plasmids, which increase the copy number by a factor of 10–30. Alternatively, the TOP1 and TOP2 genes can be placed on centromere-based plasmids under the highly inducible GAL1 promoter. In another embodiment, the TOP1 gene is placed under the control of the highly expressed constitutive PGK1 promoter (Bjornsti et al. *Cancer Res* 1989 49:6318–6323). Various dilutions of cells from isogenic strains are then plated on glucose- or galactose-containing media and survival determined by comparison of the number of colonies capable of growing up on each media. Potential effects of growth on galactose are controlled for by including isogenic strains lacking the HO cut site region within the actin intron-containing URA3 gene (termed 0 cut site strains). Once survival frequencies are established, cells surviving on galactose plates are replica plated to FOA-containing plates. Large numbers of FOA resistant colonies are screened for changes at the URA3 locus by PCR amplification of yeast colonies. The presence or absence and the size of PCR products is determined on agarose gels. DNA is extracted from colonies of interest and analyzed by Southern blots using URA3 probes. Potential translocation events are further analyzed by additional Southern blots, and by subcloning or PCR amplifying the breakpoints, as described above, followed by sequencing.

Because overexpression of TOP2 is lethal, the protocol is modified by carrying out GAL-TOP2 and GAL-HO induction for several hours in liquid media followed by plating dilutions of the cells on YPD (rich-nonselective) media as well as FOA media. This alternative induction protocol produces results similar to those with the direct plating method. The main disadvantage is that FOA resistant colonies may not be independent. This problem can be obviated by setting up multiple independent cultures for induction and analyzing only one or a limited number of events from each culture.

From these experiments, survival of isogenic strains as a function of level of topoisomerase expression are compared. Since cell survival in this system is mostly dependent on nonhomologous recombination, data from these experiments also provides an indication of potential effects of topoisomerases on nonhomologous repair pathways. After analyzing survival, the frequency and spectrum of FOA resistance amongst survivors is also determined. The background contribution of inactivating point mutations in the URA3 coding region is assessed by determining the frequency of FOA resistance in the 0 cut site control strain and by determining the fraction of PCR products whose sizes are unchanged from the original. The spontaneous frequency of FOA resistance in different strain backgrounds is compared to determine whether any of the alterations result in a mutator phenotype. By comparing the frequency and spectrum of FOA resistant events in different isogenic strain backgrounds, specific repair pathways being utilized can be determined.

Finally, the junctional sequences can be determined. Since the sequence of the entire yeast genome is readily available, identification of one translocation breakpoint provides the information necessary for identification of the reciprocal breakpoint through the use of appropriate PCR primers. By determining the choice of partners and the specific sequences present at each breakpoint, potential translocational hotspots can be identified along with information concerning the specific joining mechanisms involved in the repair. Breakpoint sequences are compared to consensus topo1 and topo2 recognition and cleavage sites to see if there is a correlation, and whether more specific consensus sequences can be identified (Capranico, G. and Binaschi, M. Biochim Biophys Acta 1998 1400:185–194).

Cell systems of the present invention may also be useful in assessing cancer chemotherapeutic agents such as those that target topoisomerases to assess affects on the frequency and type of chromosomal rearrangements. Drugs that target topoisomerases are amongst the most commonly used cancer chemotherapeutic agents. Many of these drugs act by stabilizing the nicked or broken protein-DNA intermediate (the "cleavable complex") and by interfering with the subsequent resealing step. Topo II inhibitor drugs such as etoposide and VP16 have been strongly implicated as the causative agents in treatment-related leukemias, a tragic complication of cancer therapy. With the present invention, the role of both topo I and topo II inhibitor drugs on the formation of translocations in yeast can be assessed.

The yeast based assay of the present invention is particularly well suited for analyzing the effects of drugs which poison topoisomerases on the formation of chromosomal rearrangements. As will be obvious to those of skill in the art upon this disclosure, however, this assay could also be used to assess chromosomal rearrangements caused by other pharmacologic agents, referred to herein as "drugs" or test drugs". Using drug sensitive yeast strains multiple classes of drugs can be tested, as well as multiple analogs of particular drugs, to determine their toxicity, their relative ability to form translocations, and to analyze the nature of the chromosomal rearrangements they cause. These types of studies are invaluable for understanding the mechanisms of actions of particular drugs, for characterizing their deleterious side effects, and for identifying new drugs which may have altered activities with regard to translocation formation. The assay can also be used to assess chromosomal rearrangments associatd with other chemical agents.

These experiments are conducted with no test drug, a low concentration of test drug (i.e. below the threshold for viability effects), and a high concentration of test drug (i.e. at a level which results in approximately 25–50% survival). These different concentrations of drug are chosen because it is plausible that the drug effects are in part direct and in part indirect. For example, low levels of test drug may induce a cellular response that could affect rearrangements in an indirect way, whereas at high drug concentrations the high frequency of chromosomal breaks could directly affect translocation formation. These differences may become apparent by detailed comparison of the spectrum of rearrangements.

The effects of the test drugs are compared in isogenic strains, i.e. those which either do or do not overexpress TOP1 or TOP2 and which do or do not carry mutations which increase drug uptake and reduce drug efflux. The lethal concentrations of the test drugs are determined under two sets of conditions: 1) dilutions of cells are grown on plates containing various concentrations of the drugs, and 2) cells are grown in liquid culture with different concentrations of the drugs for various lengths of time, before washing out the drug and plating on rich media plates. For initial studies, it is preferred that strains which contain URA3::actin intron without the HO cut site (i.e. 0 cut site strains) be used and that the cells be grown in the presence of either galactose or glucose. From these initial studies, the preferred range of drug concentrations to use in additional experiments with various strains is determined. It will then be determined whether the presence of topoisomerase poisons affects the frequency of survival, the frequency of chromosomal rearrangements, and the spectrum of chromosomal rearrangements, after inducing a DSB at the URA3::actin intron::HO cut site locus.

The effects of drugs on translocation formation using different sources of enzymes can also be determined. For example, it has been demonstrated that human DNA topoisomerase II alpha and II beta (Ishida et al. *Cancer Res.* 1995 55:2299–2303; Wasserman et al. *Cancer Res.* 1993 53:3591–3596), as well as human DNA topoisomerase I (Bjornsti, et al. Cancer Res. 1989 49:6318–6323) can all functionally complement yeast topoisomerase deletions. Using the system of the present invention, it can be determined whether the response to drugs, in terms of viability or spectrum of rearrangements, is specific to the source of the enzyme. In terms of using this assay for studying cancer-causing translocations, the data obtained using the human enzyme is particularly important, especially if these results are quantitatively or qualitatively different from those obtained with the yeast enzymes.

These cell systems can also be used to determine whether particular hotspots for human tumor-related translocations on chromosome 11q23 are retained in yeast. For example, an 8.3 kb region from the human MLL locus, which is known to be a hotspot for chromosomal translocations in treatment-related and infant-onset leukemias can be introduced into a yeast cell system of the present invention. Specifically, the 8.3 kb BamH1 fragment from the MLL locus is inserted into the yeast genome at the LYS2 locus on chromosome II. With this new strain, experiments similar to those discussed above are carried out, using yeast or human TOP2, a variety of expression conditions, as well as different topo II inhibitor drugs. Changes in the frequency or spectrum of FOA resistance due to the presence of this fragment are assessed. In addition, PCR primers flanking the breakpoint cluster region (bcr) are made to screen large numbers of FOA resistant cells for translocations between the URA3 locus and the MLL locus. Accordingly, using the assay of the present invention, the properties of this domain in yeast are analyzed to determine the basis for its association with cancer-causing translocations.

This assay can also be used as a genetic screen to identify host genes which play a role in maintaining chromosomal stability in general and in suppressing translocation formation in particular. This can be accomplished using routine insertional mutagenesis techniques (Burns et al. *Genes and Dev.* 1994 8:1087–1105; Ross-MacDonald et al. *Proc. Natl. Acad. Sci. USA* 1997 94:190–195). With this technique, non-essential genes can be randomly disrupted and uniquely marked. Large numbers of mutagenized colonies are collected, patched and replica plated to galactose containing plates, followed by plating to FOA-containing media. By comparing the number of resistant papilla that appear on different patches to non-mutagenized controls, candidate mutants that have increased frequencies of FOA resistance can be detected. These candidates are then secondarily tested on glucose media to determine if this represents a general mutator phenotype, and the URA3 locus of the papillae is examined by PCR to determine the nature of the resistance events. The disrupted gene in candidates of interest is identified by rescuing the transposon insertion plus flanking yeast DNA back into *E. coli*. In addition to characterizing the nature of these rearrangements, it can also be determined if there are human homologs to these genes. These human genes could represent candidates for cancer predisposition genes.

While experiments described herein are based primarily upon the URA3::actin intron assay in yeast, as will be obvious to those of skill in the art upon this disclosure, modifications can be made to provide for an assay with greater versatility and a higher yield of translocations rather than homologous repair or Ty1 insertional repair events. For example, data disclosed herein demonstrate that multiple repair pathways are operating and potentially competing in yeast cells for repair of the DSB. In particular endogenous Ty1 cDNAs can be inserted at the breaks. These endogenous products are present in yeast cells since Ty1 is present at approximately 35 copies per genome and is highly transcribed and translated. Thus, for chromosomal translocation analysis, it may be preferred to eliminate this competing reaction to increase the yield of chromosomal rearrangements. Transcription of endogenous Ty1 elements can be virtually eliminated by a mutation in the SPT3 gene (Boeke et al. *Mol. Cell. Biol.* 1986 6:3575–3581; Winston et al. *Cell* 1984 39:675–682; and Winston, F. and Minehart, P. L. *Nucleic Acids Res.* 1986 14:6885–6900). This gene encodes a non-essential transcription factor that is required for efficient transcription of Ty1. Aside from a defect in mating and sporulation, spt3 strains are generally healthy. The SPT3 gene is functionally inactivated using a two step gene replacement protocol and a mutant SPT3 allele.

Alternatively, the endogenous actin intron can be deleted from the strains. A repair event that appeared as a deletion by the PCR assay was observed in both WT and ku80 strains. For WT this occurred in 1/12 FOA$^r$ colonies examined; in ku80 it occurred in 72/80 colonies examined. In each case the amplified PCR product covering the URA3::actin intron::HO cut site region was approximately 130 bp smaller than the parent product. Sequence analysis showed that the HO cut site region was precisely removed. Examination of the upstream URA3::actin intron junction revealed that the splice donor was still present, but that the 12–16 junctional bases of URA3 had been replaced by an actin exon sequence. This replacement changes the reading frame of the URA3 mRNA. Homologous recombination is initiated by strand invasion of a DNA duplex by a homologous DNA single-strand (Szostak et al. *Cell* 1983 33:25–35). Because 130 bases of unique MAT sequence flank the HO cut site, the sequences homologous to the ACT1 locus are relatively hidden and do not contribute significantly to the repair, as is seen by the similar survival frequencies for the WT and rad52 single cut site strains. However, as seen from the experiments described herein, in strain backgrounds where the homologous recombination pathway is still functional, aberrant homologous repair events can be detected. The ratio of precise homologous repair events (FOA$^S$) to aberrant events (FOA$^R$) has not been determined, but the presence of the homologous actin intron sequences at ACT1 represents an alternative repair pathway that can also be eliminated to increase the yield of chromosomal rearrangements in the assay. This is accomplished by specifically deleting the intron region of ACT1 gene using a two step gene replacement procedure (Rothstein, R. *Methods Enzymol.* 1991 194:281–301). Specific deletion of the actin intron from the single copy ACT1 gene has no effect on viability or cellular function.

A diploid version of the URA3::actin intron assay can also be created. The assay used in the experiments described herein employs a haploid yeast strain. While this provides a strong selection for survival, it also limits the potential partners for translocation events to intergenic regions and to non-essential genes. Translocations involving breakpoints in essential genes cannot be detected because such cells will not survive. Therefore it would be advantageous to develop a related assay in a diploid strain. Numerous studies have demonstrated that ploidy may play a role in the repair response of an organism (Astrom et al. *Nature* 1999 397:310). In addition, the diploid system is more similar to the human situation and allows for more complex chromosomal rearrangements.

Figure 2:
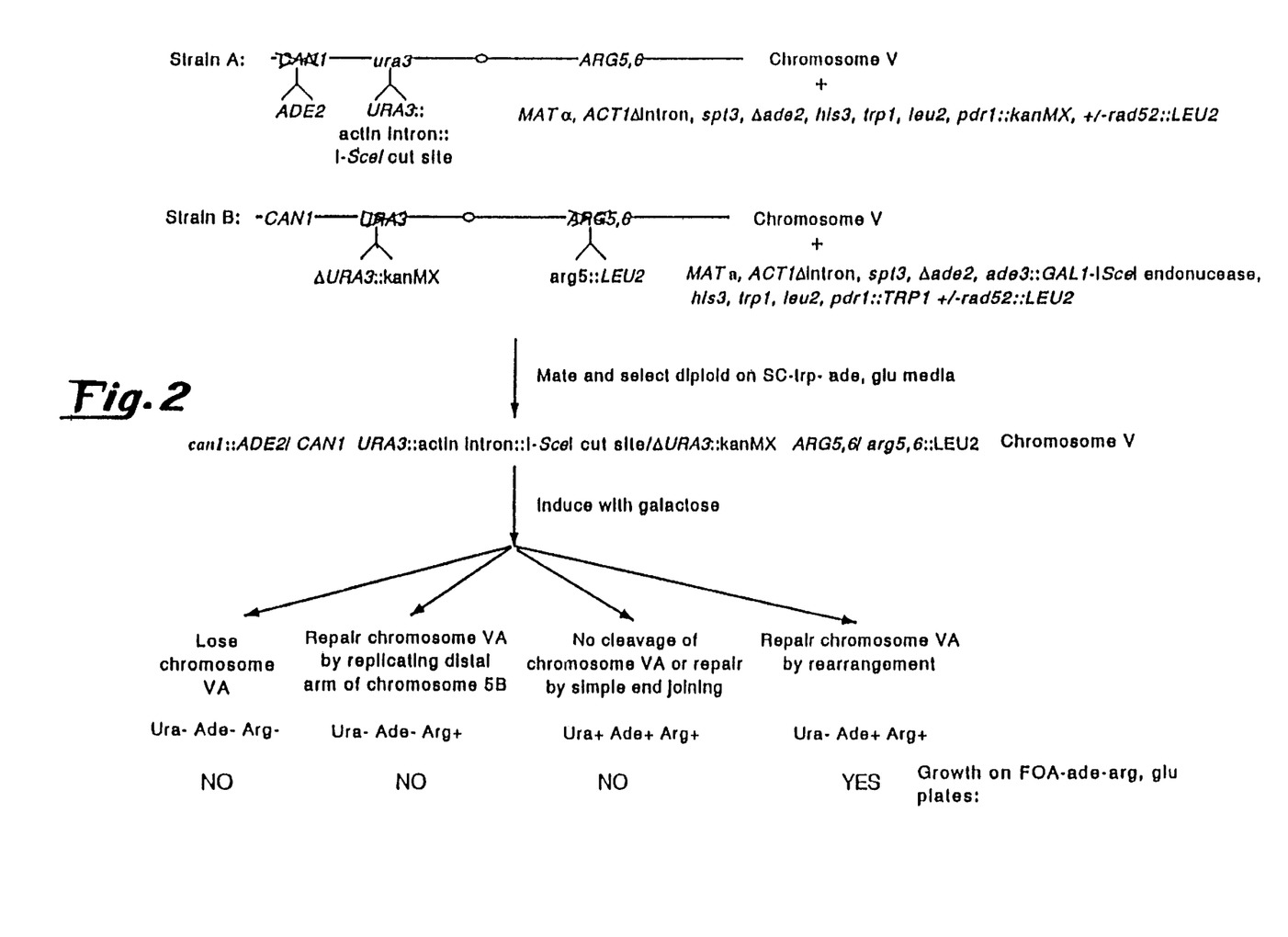
FIG. 2 provides a schematic of a diploid, yeast based assay of the present invention.

Because yeast cells can tolerate aneuploidy, chromosome loss (2n−1) after a DSB must be distinguishable from chromosome retention or translocation. As shown in FIG. 2, in a diploid assay the strains are set up so that the two homologs of chromosome V are distinguishable by a series of marker genes. For example, on chromosome VA, the URA3 gene is modified by the addition of actin intron into which is placed the I-SceI cut site. This is the test chromosome, similar to that of the haploid assay, except that a different site-specific endonuclease is used. This change is necessitated by a requirement for intact mating type genes at the MAT loci. A complete deletion of the URA3 gene is made on chromosome VB, so that there is no homology with which the DSB on VA can be repaired. This complete deletion is made using the kan MX gene disruption system (Wach et al. *Yeast* 1994 10:1793–1808). In the diploid strain, after induction of I-SceI endonuclease, the cells can become FOA$^R$ (i.e Ura–) either by loss of chromosome VA (2n–1 aneuploidy) or by repair of the break via translocation or some other chromosomal rearrangement. Based on studies of the fate of broken chromosomes in diploid strains (Kramer et al. *Mol. Cell. Biol.* 1994 14:1293–1301; Malkova et al. Proc. Natl. Acad. Sci., *USA* 1996 93:7131–716; Sandell, L. L. and Zakian, V. A. *Cell* 1993 75:729–739), it is expected that in the absence of homologous recombinational repair, the major fate of the broken chromosome VA will be chromosome loss. Thus, loss events will need to be screened out so that rearrangement events can be identified via a series of markers on chromosome V.

For example, a functional copy of the ADE2 gene can be inserted onto the distal left arm of chromosome VA at the CAN1 locus. No other copies of ADE2 are present in either strain A or strain B. The ADE2 gene serves as the major marker of chromosome VA retention after a DSB. This can be monitored in two ways, depending on the application. By plating induced cells on FOA-adenine media, only cells which have repaired chromosome VA will grow. Alternatively, a color assay can be used, since ade2 cells grows as red colonies on media with limiting concentrations of adenine, while cells which retain the ADE2 gene grow as white colonies.

Retention of chromosome VA is also monitored by disrupting the ARG gene located on the right arm of chromosome 5B. Deletion of this non-essential gene renders the cells auxotrophic for arginine. By growth on media lacking arginine, only cells which have retained the right arm of chromosome VA are capable of growth.

In addition to these modifications, the basic strain also preferably has the following properties: Both strains A and B are spt3 so that endogenous Ty1 insertions do not make up a significant portion of the FOA resistant rearrangement events. Strain B contains an insertion of the GAL1-inducible I-SceI gene at the ADE3 locus so that I-SceI endonuclease are expressed at high levels by growth on galactose. The ADE3 gene is wild type in strain A, so that the ADE2 color marker system can be utilized in both the haploid strain A and in the diploid strain. Additionally, both haploid strains are made deficient for the PDR1 gene. This will make the strain sensitive to drugs in the media and allow for testing the effect of different chemical agents on rearrangements. If the presence of homologous chromosomes causes too high a background of homologous repair events, rad52 can also be disrupted in these strains to entirely eliminate this repair pathway.

Yeast cells have been observed to be relatively resistant to many drugs, as a result of impermeability and/or active systems mediating drug efflux. However, several mutant yeast strains with increased sensitivity to anti-topoisomerase agents have been identified. In particular ISE1 (also known as ERG6) encodes a nonessential protein involved in yeast cell membrane biosynthesis. Deletion of ISE1 results in pleiotropic sensitivity to several drugs including camptothecin, aphidocholin and cycloheximide (Nitiss, J. and Wang, J. C. *Proc. Natl. Acad. Sci. USA* 1988 85:7501–5). In a screen for yeast mutants with altered sensitivity to camptothecin, PDR1 was identified (Reid et al. *J Biol Chem* 1997 272:12091–12099). This gene encodes a nonessential transcription factor which regulates a large number of genes involved in "pleiotropic drug resistance", including transporters related to mammalian multidrug resistance (MDR1) genes. Thus, to examine the effect of different drugs on translocation formation in this assay, either or both of these genes are disrupted using standard disruption protocols. Cells are then assayed for camptothecin hypersensitivity as a phenotypic marker of the gene inactivation. These strains will then be crossed into the above described strains and used to analyze survival and FOA resistance as a function of drug concentration.

The intron-based assays of the present invention used in studying translocation formation need not be limited to yeast. Similar systems can be generated in mammalian culture cell systems including humans. For example, using hemizygous APRT human cell lines engineered to contain a cut site within an intron, and a tetracycline inducible I-SceI vector, aprt-cells can be selected after tetracycline induction. Using FISH analysis, translocations can then be screened for by simultaneously analyzing the proximity of genes flanking APRT on chromosome 16. Mammalian cells can be wild type or mutant for genes of interest such as, but not limited to, oncogenes or tumor suppressor genes. Using FISH analysis, PCR, Southern blots, sequencing and database analysis, other types of rearrangements can also be characterized.

Further, while the assay in these experiments utilizes an HO endonuclease recognition sequence to create a DSB which is then repaired in a way yielding FOA resistance, other endonuclease/recombinase recognitions sites could be used in place of the HO cut site. Any number of rare cutting endonucleases can be substituted. Examples include, but are not limited to, I-SceI, FLP recombinase and I-Ppo. Further, any inducible promoter (e.g. the tetracycline-inducible or repressible promoter Tet system) can be substituted for the GAL1 promoter.

Alternatively, random DNA sequences could be used in the same location to determine if they represent naturally occurring or even drug-induced breakage sites. Any DNA sequence which acts as a target for any number of enzymes, drugs, or protein factors (e.g. site-specific recombinases, topoisomerases, transcription factors with specific DNA binding domains) can be inserted within the intron and tested for its effect on chromosomal stability as long as the presence of these sequences do not interfere with intron splicing and consequently affect expression of the marker gene. One advantage to this type of approach is that different types of breaks at URA3 resulting in various types of repair events can be determined. Further, preferred translocation partners within the yeast genome and their dependency on the nature of the initial cleavage event can be determined.

In addition, while the URA3 gene was used in these experiments, any gene (e.g. LYS2 in yeast, adenine phosphoribosyltransferase (APRT) or thymidine kinase (TK) in human cells) whose absence of expression can be selected for (i.e. counterselection) can be used. Similarly, while the actin intron was used in these experiments, any sequence recognized by the eukaryotic organisms splicing apparatus as an intron, either natural or artificial, can be substituted for the actin intron.

While survival is used as the initial criteria for potential repair events in experiments described herein using haploid yeast cells, in diploid cells chromosome retention or loss after induction a DSB can be assayed for using appropriate dominant marker genes placed on the arms of the chromosome with the intron-containing marker gene. These considerations are of particular importance when extrapolating to higher eukaryotes such as human cells, which are normally diploid. These additional dominant markers could be, for example, drug-resistance genes (e.g. G418 or hygromycin resistance) or color markers (b-galactosidase, b-glucuronidase, ADE2, or green fluorescent protein).

Finally, although the yeast strains described have only particular defined mutations, any yeast gene can be specifically mutated by standard methods in order to determine the effect of this mutation on chromosome stability using this assay. Further, any yeast gene can be overexpressed by standard methods to determine the effect of specific gene overexpression on chromosome stability using this assay. Any sequence of DNA can be integrated at specific sites in the yeast genome or brought into the yeast in a plasmid or YAC, using standard yeast methods, to determine the effect of their presence on chromosome stability. Finally, yeast can be randomly mutated to screen for genes whose altered activity has an effect on chromosome stability.

The following nonlimiting examples are provided to further illustrate the present invention.

EXAMPLES

Example 1

Construction of URA3::actin intron::HO Cut Site Strains

The prototype *Saccharomyces cerevisiae* (referred to herein as yeast) strains used for these experiments (AGY116=1 cut site strain=ho, Δhml::ADE1, Δmata::hisG, Δhmr::ADE1, ade1, LEU2, lys5, trp1::hisG, ade3::GAL-HO, URA3::actin intron::MATa cut site region; AGY112=2 cut site strain=ho, Δhml::ADE1, Δmata::hisG, Δhmr::ADE1, ade1, leu2::MATa cut site region, lys5, trp1::hisG, ade3::GAL-HO, URA3::actin intron::MATa cut site region; AGY150=0 cut site strain=ho, Δhml::ADE1, Δmata::hisG, Δhmr::ADE1, ade1, LEU2, lys5, trp1::hisG, ade3::GAL-HO, URA3::actin intron) were all derived from strain YFP17 (=ho, Δhml::ADE1, Δmata::hisG, Δhmr::ADE1, ade1, leu2::MATa cut site region, lys5, trp1::hisG, ade3::GAL-HO, ura3-52) "ho" refers to the fact that the endogenous HO endonuclease is non-functional.

The essential modification of the original YFP17 strain was replacing the ura3-52 allele on chromosome V with a URA3::actin intron::+/−MATa cut site cassette (referred to herein as URA3::actin intron::HO cut site). This was accomplished in several steps, as follows:

First, a 308 bp PCR product comprising the endogenous yeast actin intron was created using primers RAG337: 5'GATC<u>TACGTA</u>TGTTCTAGCGCTTGCAC3' (SEQ ID NO: 1) and RAG338: 5'GATC<u>TAGCTA</u>AACATATAATATAGCAAC3' (SEQ ID NO: 2) and genomic yeast DNA as the template. These PCR primers were designed so that the resulting PCR product could be cut with SnaBI and AluI (underlined bases) to create blunt ends precisely at the canonical splice donor GT and splice acceptor AG sequences of the actin intron. The 308 bp digested PCR product was digested with SnaBI and AluI and ligated to StuI digested plasmid YDp-U 1. YDp-U consists of a pUC9 vector plus the 980 bp BamHI fragment containing the *S. cerevisiae* URA3 gene. StuI digestion of URA3 was chosen because it creates a blunt cut at position 435 in the URA3 gene relative to the URA3 initiation codon. The orientation and sequence of the resulting intron insertion was confirmed by restriction digestion and sequencing of the exon-intron junctions using primers RAG444: 5'TGT-TAGCGGTTTGAAGCAGG3' (SEQ ID NO:3) in the URA3 gene upstream of the StuI site, as well as RAG445: 5' TTCTCCAGTAGATAGGGAGC3' (SEQ ID NO:4) in the URA3 gene downstream of the StuI site. This intermediate plasmid was called AGE1611.

The 1288 bp BamHI fragment containing the URA3::actin intron from AGE1611 was then subcloned into the BamHI site of plasmid AGE1612. AGE1612 is the HIS3 marked centromere based yeast shuttle vector plasmid pRS413 (described by Sikorski, R. S. and Hieter, P. *Genetics* 1989 122:19–27) modified by filling in the unique XhoI site in the polylinker with Klenow polymerase+dNTPs. The resulting plasmid was called AGE1638. AGE1638 was transformed into a his3− ura3− yeast strain and shown to confer both uracil and histidine prototrophy, thereby demonstrating that the presence of the actin intron did not interfere with the expression and functioning of the modified URA3 gene.

Next, a PCR product consisting of the 149 bp region surrounding the HO cut site present at the MATa locus was subcloned into the unique XhoI site of AGE1638. This XhoI site is located within the actin intron, 62 bp from the splice donor site. This was accomplished by PCR amplification of the endogenous MATa sequence using primers RAG486: 5'CCCGGAGCTCGAGCTC-GATCTAAATAAATTCGTTTTCAATG3' (SEQ ID NO:5) and RAG487: 5'GGGCGAGCTCGAGCTCAACCACTC-TACAAAACC3' (SEQ ID NO:6), cleaving this PCR product with Xho1 and ligating it to phosphatase-treated XhoI-digested AGE1638. The orientation and sequence of the resulting plasmid, termed AGE1662, was confirmed by digestion with BstNI, and by sequencing. It was also confirmed that the addition of the 132 bp HO cut site region did not interfere with URA3 expression by transforming AGE1662 into his3− ura3− yeast and demonstrating conversion to histidine and uracil prototrophy.

The yeast strains described supra were then constructed by integrating the URA3 containing BamHI fragment from either AGE1638 or AGE1662 into strain YFP17 and selecting for uracil prototrophy. Integration of the cassette at the URA3 locus was confirmed by PCR using two pairs of primers, either RAG512: 5'GCGAGGCATATTTATGGT-GAAGG3' (plus strand in the flanking DNA upstream of the URA3 locus; SEQ ID NO:7) and RAG514: 5'GTACAT-GAGACTTAGTAACAGTAGC3' (minus strand of the actin intron, downstream of the XhoI site; SEQ ID NO:8)) and RAG513: 5'ATGTTCTAGCGCTTGCACCATC3' (plus strand of the actin intron, upstream of the XhoI site; SEQ ID NO:9) and RAG515: 5'GGAGTTCAATGCGTCCATC3' (minus strand in the flanking DNA downstream of the URA3 locus; SEQ ID NO:10).

For strain AGY112 (2 cut site strain) the BamHI fragment from AGE1662 was integrated into YFP17.

For AGY116 (1 cut site strain), YFP17 was first modified by integrating a wild type LEU2 gene at the leu2::HO cut site locus on chromosome III, using the LEU2-containing BamHI fragment in plasmid YDP-L (described by Berben et al. *Yeast* 1991 7:475–477). This eliminates the pre-existing HO cut site at the LEU2 locus and converts the leucine auxotrophic strain to leucine prototrophy. This intermediate strain is called AGY104. The URA3::actin intron::HO cut site cassette from AGE1662 was then used to transform AGY104 to uracil prototrophy as described for AGY112.

For strain AGY150 (0 cut site strain), strain AGY104 was transformed with the BamHI fragment from AGE1638, and uracil prototrophs were selected. This creates a URA3::actin intron allele which acts as a negative control for chromosome cutting.

Example 2

Determination of Frequency of Cell Survival, FOA Resistance, and the Spectrum of Chromosomal Alterations after HO Endonuclease Cleavage of the URA3::actin intron::HO Cut Site Locus Liquid cultures of various yeast strains were grown at 30° C. in rich media (YP) containing raffinose as the sole carbon source to a cell density of approximately $2 \times 10^7$ cells per ml. Cells were diluted and spread on either YP-dextrose or YP-galactose plates, containing 1% bacto agar and incubated at 30° C. for 3–5 days. Colonies were counted and the survival frequency was calculated by determining the number of colonies growing per ml on galactose containing plates divided by the number of colonies growing per ml on glucose containing plates. Plates containing colonies growing on galactose were replica plated to synthetic complete glucose plates supplemented with 5-fluoro orotic acid (FOA) as described by Boeke et al. Molec. Gen. Genet. 1984 197:345–346 and Sikorski et al. Methods Enzymol. 1991 194:302–329. Colonies growing on this media were counted and the ratio of colonies growing on FOA to those growing on YP-galactose was calculated to determine the frequency of FOA resistance. Individual colonies on the FOA plate were picked and grown to saturation in liquid YP-dextrose media at 30° C., and then genomic DNA was extracted by the phenol-glass bead method as described by Hoffman, C. S. and Winston, F. *Gene* 1987 57:267–272. Genomic DNA was then used as template for PCR reactions to screen for changes around the HO cut site. For this screen, the PCR primers were on either side of the HO cut site, within the URA3 gene segments and consisted of RAG444: 5'TGTTAGCGGTTTGAAGCAGG3' (SEQ ID NO:3) and RAG445: 5'TTCTCCAGTAGATAGGGAGC3' (SEQ ID NO:4) which are upstream and downstream of the StuI site in URA3. In some cases the PCR products were then sequenced using primers RAG513: 5'ATGTTCTAGCGCTTGCACCATC3' (SEQ ID NO:9) and RAG633: 5'TTTCAAGCCCCTATTTATTCC3' (SEQ ID NO:11). In cases where no PCR product was obtained because of large-scale chromosomal rearrangements, the sequences which bordered the HO cut site were determined using inverse PCR as described by Ochman et al. *Genomics* 1988 120:621–623. For this procedure, genomic DNA was cut with NsiI which cuts in flanking DNA sequences as well as in URA3, downstream of the HO cut site. After phenol extraction of the digested genomic DNA, it was religated under dilute conditions to favor intramolecular ligations, and the products were PCR amplified using primers RAG613: 5' AGCGTCTGCTCTAGCGTTAC3' (SEQ ID NO:12) and RAG444 or RAG614:5'GTAGAGGGTGAACGTTACAG3' (SEQ ID NO:13) and RAG445. Sequencing of the PCR product obtained was then done with either RAG513 or RAG619:5'CAGTCAATATAGGAGGTTATG3' (SEQ ID NO:14). Once the flanking sequence was obtained, its unique location within the yeast genome was determined by searching the Saccharomyces genome database (http://genome-www.stanford.edu/Saccharomyces/).

What is claimed is:

1. An assay for detecting and characterizing chromosomal rearrangements in eukaryotic cells comprising:
    (a) genetically engineering a eukaryotic cell to contain a selectable/counter-selectable marker gene with a site for generating a double strand break within an intron of the eukaryotic cell;
    (b) generating the double strand break;
    (c) detecting cells which repair the double strand break by chromosomal rearrangements;
    (d) isolating DNA from the detected cells; and
    (e) characterizing the chromosomal rearrangement as a nonhomologous translocation, inversion, deletion or insertion.

2. The assay of claim 1 further comprising exposing the genetically engineered eukaryotic cells to an environmental factor prior to or concurrent with generating the double strand break so that effects of the environmental factor on chromosomal rearrangement can be determined.

3. The assay of claim 2 wherein the environmental factor is a drug, test drug or chemical agent.

4. The assay of claim 1 wherein a selected gene of the eukaryotic cells is mutated or overexpressed so that effects of mutating or overexpressing the selected gene on chromosomal rearrangement can be determined.

5. The assay of claim 1 wherein the genetically engineered eukaryotic cells comprise yeast cells containing a URA3 gene with an HO endonuclease recognition site within an actin intron of the yeast cells and the double strand break is generated by inducing expression of HO endonuclease in the yeast cell.

6. The assay of claim 5 further comprising exposing the yeast cells to an environmental factor prior to or concurrent with generating the double strand break so that effects of the environmental factor on chromosomal rearrangement can be determined.

7. The assay of claim 6 wherein the environmental factor is a drug, test drug or chemical agent.

8. The assay of claim 5 wherein a selected gene of the yeast cell is mutated or overexpressed so that effects of mutating or overexpressing the selected gene on chromosomal rearrangement can be determined.

\* \* \* \* \*